United States Patent [19]

Pfeiler

[11] 4,398,302
[45] Aug. 9, 1983

[54] X-RAY DIAGNOSTIC SYSTEM COMPRISING A RADIOGRAPHIC UNIT WITH AN X-RAY TUBE WHICH CAN EMIT A FAN-SHAPED RADIATION BEAM

[75] Inventor: Manfred Pfeiler, Erlangen, Fed. Rep. of Germany

[73] Assignee: Siemens Aktiengesellschaft, Berlin & Munich, Fed. Rep. of Germany

[21] Appl. No.: 207,697

[22] Filed: Nov. 17, 1980

[30] Foreign Application Priority Data

Dec. 21, 1979 [DE] Fed. Rep. of Germany ....... 2951857

[51] Int. Cl.³ .............................................. G03B 41/16
[52] U.S. Cl. ...................................... 378/146; 378/99
[58] Field of Search ................................ 378/146, 159

[56] References Cited

U.S. PATENT DOCUMENTS

| | | | |
|---|---|---|---|
| 3,101,407 | 8/1963 | Shipman | 378/146 |
| 3,717,768 | 2/1973 | Edholm | 378/159 |
| 3,766,387 | 10/1973 | Heffan | 378/146 |
| 4,315,146 | 2/1982 | Rudin | 378/146 |

Primary Examiner—Craig E. Church
Attorney, Agent, or Firm—Hill, Van Santen, Steadman, Chiara & Simpson

[57] ABSTRACT

In an exemplary embodiment, a radiation detector for reception of the radiation emerging from the radiography subject delivers electric output signals corresponding to the received radiation profile, a scanner device rotates the radiographic unit about an axis which passes through the focus of the x-ray tube and approximately through the detector center, and a measured value processing and display unit determines and reproduces the x-ray shadow image corresponding to the scanning movement of the radiographic unit (1, 4). The processing and display unit is designed in the manner of a radar display apparatus in which a number of concentric image point circles are recorded, each of which, (for the case of a radiation detector consisting of a series of individual detectors), is locally associated with a specific individual detector and is modulated in its intensity corresponding to the output signals of the associated individual detector.

7 Claims, 3 Drawing Figures

X-RAY DIAGNOSTIC SYSTEM COMPRISING A RADIOGRAPHIC UNIT WITH AN X-RAY TUBE WHICH CAN EMIT A FAN-SHAPED RADIATION BEAM

BACKGROUND OF THE INVENTION

The invention relates to an x-ray diagnostic system comprising a radiographic unit with an x-ray tube, which can emit a fan-shaped radiation beam, a radiation detector for reception of the radiation emerging from the radiography subject, which detector delivers electric output signals corresponding to the received radiation profile, means for generating a relative movement between the support device for the radiography subject, on the one hand, and the radiation beam, on the other hand, and a measured value converter and display unit, which determines and reproduces the x-ray shadow image, corresponding to the movement range, from the detector output signals.

An x-ray diagnostic system of this type is described in U.S. Pat. No. 3,101,407. In the case of this x-ray diagnostic system, the radiographic unit, comprised of the x-ray tube and radiation detector, is moved in the longitudinal direction of patient support such that an x-ray shadow image can be constructed from the output signals of the radiation detector. An x-ray fluoroscopy is only incompletely possible with this system, since a very rapid back and forth movement of the radiographic unit is necessary for an x-ray fluoroscopy, which is, in practice, difficult to realize.

SUMMARY OF THE INVENTION

The object underlying the invention resides in providing an x-ray diagnostic system of the type initially cited such that a rapid movement of the radiographic unit, and hence x-ray fluoroscopy, is possible also in case of utilization of a radiation detector having a series of individual detectors; i.e., such that a continuous image production is possible.

In accordance with the invention this object is solved in that the movement is a rotational movement about an axis which passes through the focus of the x-ray tube and the radiation detector, that the display unit is designed in the manner of a radar display unit in which a number of concentric image point circles is recorded, each of which is associated, via a transmission network, with a specific radiation detector location, and is modulated in its brightness (or intensity) corresponding to the output signal of the radiation detector at this specific detector location, and that means are present for synchronizing the recording operation with the rotational movement such that the circles are completely recorded when a scanning operation is terminated. In the inventive x-ray diagnostic system, the radiographic unit can constantly rotate with a relatively high angular velocity, such that a flicker-free fluoroscopy is possible. The radiographic unit can also be so designed that several radiation beams act on several crossed detector arrays.

The invention shall be explained in greater detail in the following on the basis of an exemplary embodiment illustrated on the accompanying drawing sheet; and other objects, features and advantages will be apparent from this detailed disclosure and from the appended claims.

DETAILED DESCRIPTION

Figure 1:
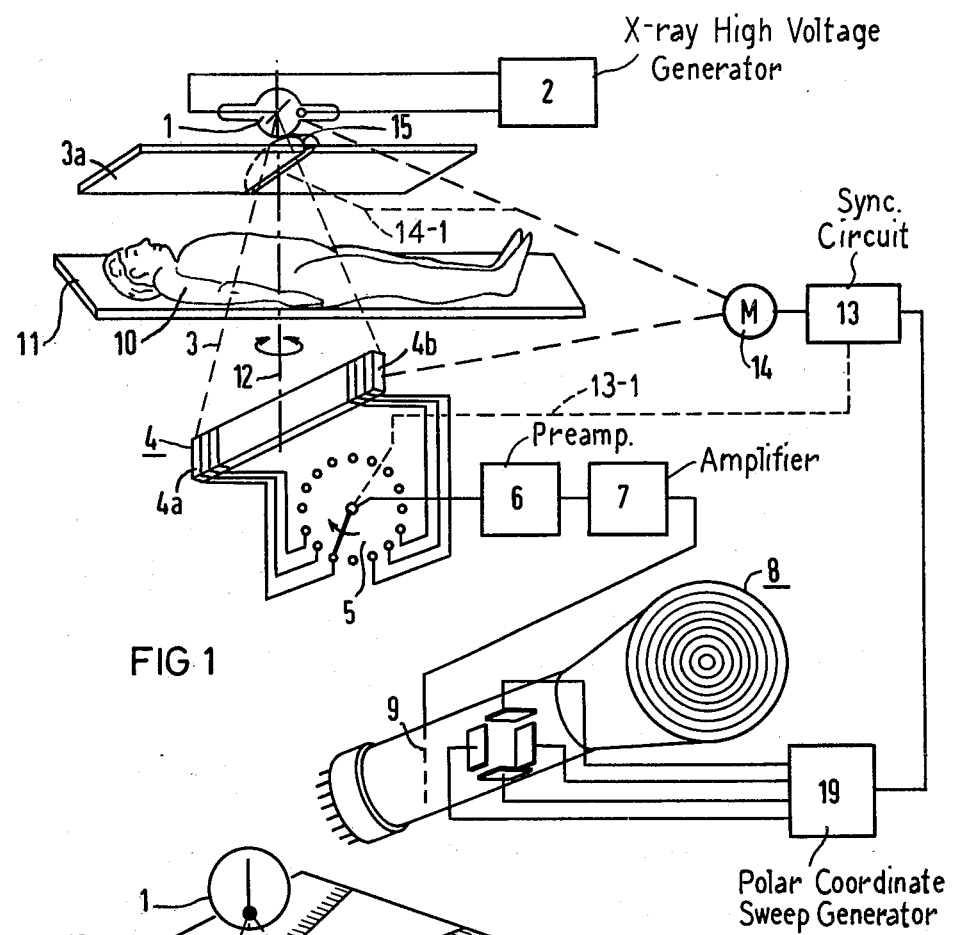
FIG. 1 illustrates an x-ray diagnostic system according to the invention.

In the drawing, an x-ray tube 1 is illustrated which is fed by an x-ray high voltage generator 2 and which emits a fan-shaped radiation beam 3 which impinges on a radiation detector 4. The radiation detector 4 consists of a series of individual detectors, each of which supplies an output signal, corresponding to the received radiation intensity, to a multiplexer diagrammatically indicated at 5. From the multiplexer 5 the signals are supplied, via a preamplifier 6 and a main amplifier 7, to a cathode ray image reproduction tube 8; namely, a control grid 9 of this image reproduction tube 8, for the purpose of intensity modulation of the scanning electron beam. The deflection voltages for the image reproduction tube 8 are generated by a sweep generator 19.

The illustrated x-ray diagnostic system serves the purpose of producing shadow images of a patient 10 lying on a support 11. For this purpose, the radiographic unit, consisting of the x-ray tube 1 and the radiation detector 4, can rotate about an axis 12 which extends through the focus of the x-ray tube 1 and approximately through the center of the radiation detector assembly 4.

The image tube 8 forms a display unit in the manner of a radar display unit in which a number of concentric image point circles is recorded (each projection being recorded at respective points along a radial scanning path of the electron beam); each image point circle is associated, via the transmission network 5, 6, 7 with a specific individual detector in the radiation detector assembly 4, and is modulated in its brightness (or intensity) corresponding to the output signal of the associated individual detector. In this manner, during continuous rotation of the radiographic unit 1, 4, there results, on the viewing screen of the picture tube 8, an x-ray shadow image which corresponds to the scanning range of the radiographic unit 1, 4. This scanning range is to be understood as that particular section from the cone, determined by the marginal (or peripheral) rays of the radiation beam 3, in which the patient 10 lies.

Through the multiplexer 5 a rapid chronologically successive transmission of the output signals of the individual detectors of the radiation detector assembly 4 to the image tube 8 takes place. This multiplexer, in practice, is of course realized electronically, as likewise the detector signals are pre-amplified and prepared for acceptance by the multiplexer e.g. via a sample-and-hold circuit which determines the time interval of each projection.

If one traces the path of an individual detector of the radiation detector assembly 4 during rotation, it is apparent that the connection line extending from the focus to the individual detector generates a conical envelope which has a base diameter corresponding to twice the distance of the individual detector from the axis of rotation 12. For data transmission from the rotating radiation detector 4 to the stationary preamplifier 6 a rotating signal coupling is necessary.

In the illustrated exemplary embodiment, as already stated above, one individual detector each of the radiation detector assembly 4 is associated with each of the circles recorded by the cathode beam of the image tube 8. The association is provided in such a manner that the outermost circle on the screen of image tube 8 is associated with the outermost detector, the next circle is associated with the detector having the next greatest distance from axis 12, and so on. Thus, the center individual detector of the radiation detector assembly 4 is associated with the innermost circle on the viewing screen of the picture tube 8. It is possible to achieve an offsetting of the individual detectors, in their respective distances from axis 12, so that actually only one individual detector is associated with every circle and the circles are uniformly spaced radially on the screen. In this case, namely, for example, the individual detectors 4a and 4b describe different orbits. The axis of rotation 12 thus does not precisely pass through the center of the detector assembly 4, but, on the contrary, through one of the individual detectors disposed closest to the detector center. In the extreme instance, one obtains a radiation detector assembly in which the center of rotation 12 lies in a marginal detector (such as 4a).

One variant of the radiation detector would be a stationarily mounted x-ray image intensifier in front of which a slit diaphragm rotates synchronously with the slit diaphragm 3a defining the x-ray beam 3. In this case, expediently, a television pickup tube, which is scanned in synchronism with the detector rotation in the illustrated exemplary embodiment; (i.e., is scanned with a raster defined by projection-rate radial scan lines and image-rate rotational scanning, synchronized with multiplexer 5 to represent the respective detector outputs along respective concentric circles) would expediently provide the signal conversion.

In both instances, naturally, the scanning of the radiography subject must be synchronized with the recording operation on the image tube, so that the circles on the image tube 8 are completely recorded when a scanning operation is terminated. For this purpose, in the illustrated exemplary embodiment, a synchronization installation 13 is provided which synchronizes the polar coordinate recording operation on the image tube 8 with the operation of a motor 14, which rotates the x-ray tube 1, the slit diaphragm 3a, and the radiation detector 4 about the axis 12. A synchronous reproduction is also to be guaranteed if the detector signals are intermediately stored for the purpose of special signal processing; e.g. in digital coding (each projection line of coded signals being stored in a line of a matrix store to readout in synchronism with the radial scan line cycle of the image tube when image display is to be effected).

Since, without primary radiation filters, the dose acting upon the central region of the patient (near axis 12) would be greater than the acting on the region of the subject remote from axis 12, a form filter 15 is arranged between the slit diaphragm 3a and the x-ray tube 1 (and in alignment with the slit). The form filter 15 thus ensures a uniform dose distribution over the extent of the radiation detector assembly 4.

If the individual detectors are broader in the azimuthal direction (transverse to the plane of the beam) than the primary radiation beam (defined by the slit of diaphragm 3a) then, directly before the radiation detector, a region corresponding to the primary radiation beam is to be diaphragmed out e.g. by suitable collimator plates, in order to keep stray radiation as remote as possible from the detector.

Figure 2:
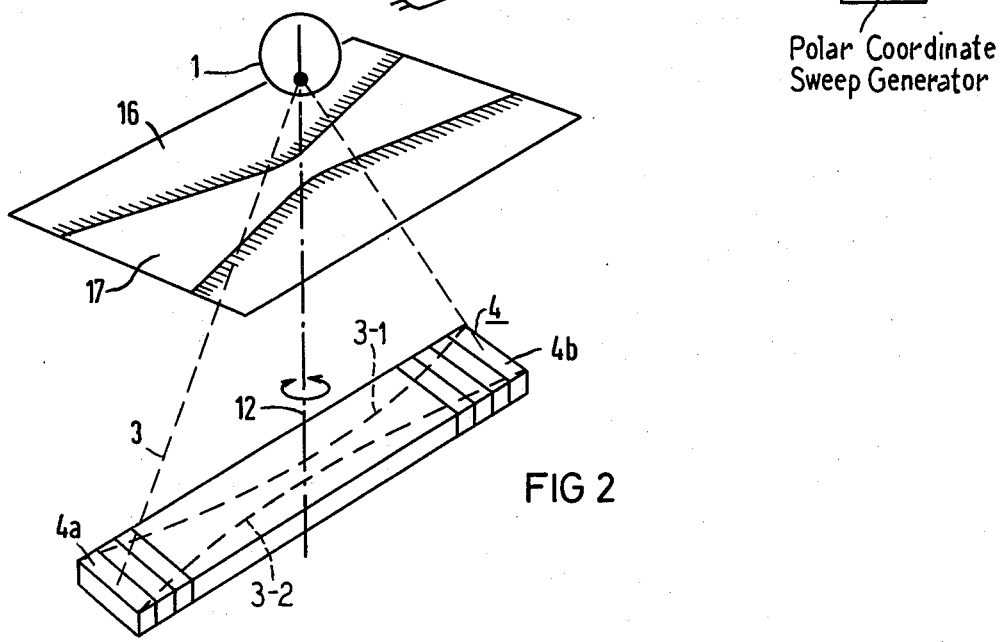
FIG. 2 illustrates a detail of the x-ray diagnostic system according to FIG. 1.

FIG. 2 illustrates the radiographic unit 1, 4 with a slit diaphragm 16 defining the primary radiation beam, which can replace the form filter 15. The slit diaphragm 16 exhibits a slit 17 for transmitting the incident radiation which is narrower in its central region than in its marginal region. In this manner, a dose compensation is likewise possible. The radiation field produced on the radiation detector 4 is illustrated in FIG. 2 by dash lines 3-1 and 3-2. If the individual detectors are broader than the radiation field whose image is formed thereon, then here also the portion of the radiation receiver 4 not impinged upon by primary radiation is to be shielded against stray radiation. In the system illustrated in FIG. 2, the azimuthal resolution decreases from the interior to the exterior. This can be countered by means of signal processing in that every signal channel, associated with an individual detector of the radiation receiver 4, receives an aperture correction signal which is dependent upon the position of the individual detector relative to the center of the radiation receiver 4.

It is also possible, instead of providing a slit in the form of an actual x-ray transmissive gap in the solid x-ray shielding material of the diaphragm, as is illustrated at 17 in FIG. 2, to provide a slit in the form of a semipermeable filter occupying a rectilinear slit region of the diaphragm whose filter effect in the slit region aligned with receiver 4, from the diaphragm center to the diaphragm edge (remote from axis 12) varies in its degree of permeability (in correspondence with the configuration of 17) such that likewise a uniform dose distribution (but over an equal width of each of the individual detectors) is obtained. Thus, for example, the density of successive increments of the length of the material of the gap region may vary so as to be greatest at the central part and least at the outer parts to provide the desired uniform dose distribution. A dose compensation is also possible by means of subdivision of an elongated, uniformly wide slit (e.g. an air gap) with the aid of x-ray impermeable lamellae (or blades) disposed transversely to the length of the slit and having a closer spacing at the central part of the slit than at the outer parts of the slit. In this manner, an image-favorable correction function can be achieved.

Figure 2A:
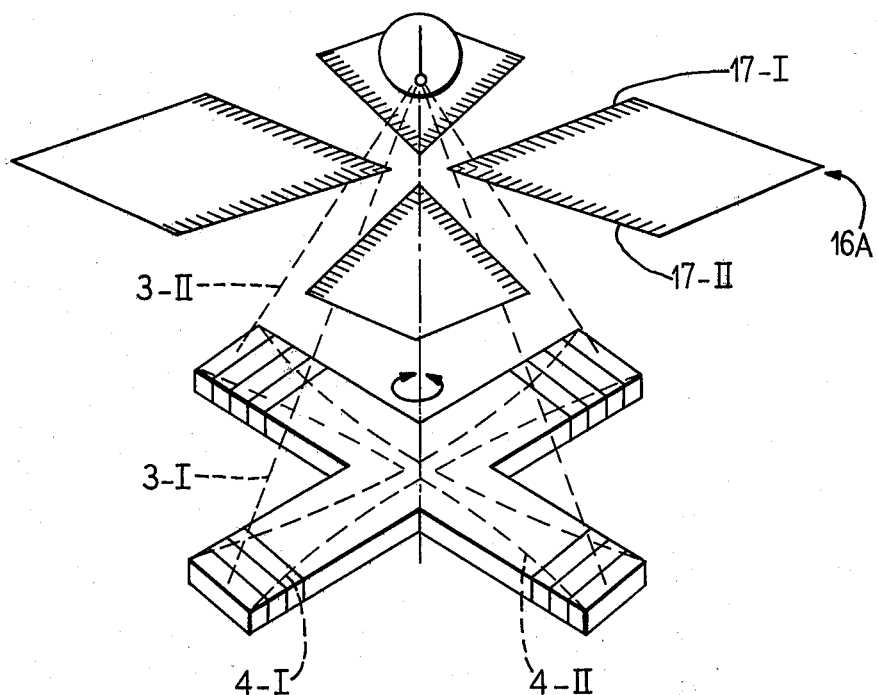
FIG. 2A illustrates a modification of the embodiment of FIG. 2.

In addition, it is possible, in utilizing several radiation beams (such as 3-I and 3-II, FIG. 2A), or radiation detectors (such as 4-I and 4-II, FIG. 2A), respectively, to equip the latter with varying width progressively (e.g. a Maltese or Formee cross configuration), in order to achieve the effect of the slit diaphragm with locally variable width; i.e., to use more radiation without introducing correction means in the signal channels or conducting only restricted corrections.

A variant consists in that the radiation detector is stationary and is formed from concentric circular series of individual detectors. The latter can be continuous or constructed from segments. Only radially slotted disks for diaphragming out of the penetrating radiation beam need rotate in this variant.

It will be apparent that many modifications and variations may be effected without departing from the scope of the novel concepts and teachings of the present invention.

SUPPLEMENTAL DISCUSSION

For the sake of diagrammatic illustration a drive of slit diaphragm 3a synchronously with detector 4 has been indicated by dash coupling line 14-1. Also operation of an electronic multiplex circuit 5 in synchronism with motor 14 has been indicated by the dash coupling line 13-1. Where the cone of x-rays from the focus of x-ray tube 1 is sufficiently uniform, or where compensation is introduced electronically in the processing circuitry 5, 6, 7, the x-ray tube may be stationary, with axis 12 aligned with the axis of symmetry of the x-ray cone from the focus. In this case, slit diaphragm 3a may be in the form of a disk with a diametric slit such as 17, FIG. 2, rotating in synchronism with the detector 4. If the multiplex sequence is as indicated at 5 in FIG. 1, sweep generator 19 may produce an active sweep along a diameter of the screen of image tube 8, the output of detector 4a, for example, being recorded at the beginning of the sweep at maximum radius in one direction, and the output of detector 4b being recorded at a slightly lesser radius in the opposite direction from the center of the screen at the end of the active sweep. The number of detector samples and of such sweeps per revolution of the electron beam could correspond to the desired resolution in the azimuthal direction at the periphery of the image tube screen. With the rate of rotation of the radiographic unit equal to the image tube beam rotation rate an interlaced scanning and display mode could be utilized by proper timing of the sampling of the detector outputs in each half revolution. A larger number of offset sub-images than two could also be employed, e.g. with a disc 16A, FIG. 2A, having crossed slits as indicated at 17-I and 17-II, of configuration such as shown at 17, FIG. 2, using two sets of memory units for alternately storing the outputs of the two detector lines (e.g. 4-I and 4-II, FIG. 2A) and for alternate supply of the stored lines to a polar scanning electron beam angularly scanning at twice the rotational rate of the dual radiographic unit.

I claim as my invention:

1. An x-ray diagnostic system comprising a radiographic unit with an x-ray source which emits a fan-shaped radiation beam; a support for a radiography subject a radiation detector for reception of the radiation emerging from the radiography subject, said detector supplying electric output signals corresponding to the received radiation profile; scanning means for producing a relative scanning movement between the support for the radiography subject and the radiation beam; and a measured value processing and display unit for receiving the detector output signals, and for determining and reproducing an x-ray shadow image corresponding to the scanning movement, said scanning means producing a rotational scanning movement about an axis (12), which passes through the focus of the x-ray tube (1) and the radiation detector (4), the measured value processing and display unit being operable for effecting a polar coordinate display wherein a number of concentric image point circles are recorded, each of which is allocated to a specific detector location of the radiation detector (4) and is modulated in its intensity corresponding to the output signal of the radiation detector (4) at this detector location, and means (13) coupled with said scanning means and with said processing and display unit for synchronization of the recording operation with the rotational movement, so that the circles are completely recorded when a scanning movement is terminated.

2. An x-ray diagnostic system according to claim 1, with said scanning means providing an axis (12) for the rotation of the radiographic unit (1, 3a, 4) which passes approximately through the center of the detector.

3. An x-ray diagnostic system according to claim 1, with an x-ray filter (15) in a primary radiation path of the radiation beam (3) which effects a uniform dose distribution on the radiation detector (4).

4. An x-ray diagnostic system according to claim 1, with a slit diaphragm (16) arranged in a primary radiation path of the radiation beam, having a slit (17) for transmitting the radiation which is narrower in its central region than in its marginal region.

5. An x-ray diagnostic system according to claim 1, with a semipermeable x-ray filter diaphragm provided in a primary radiation path of the radiation beam (3), whose filter effect varies from the diaphragm center to the diaphragm edge to provide a substantially uniform dose distribution at the radiation detector (4).

6. An x-ray diagnostic system according to claim 1, with the x-ray source emitting several fan-shaped intersecting radiation beams, and the radiation detector being a crossed detector arrangement for receiving these radiation beams.

7. An x-ray diagnostic system according to claim 1, with diaphragm means immediately before the radiation detector (4), for defining an x-ray transmissive region of configuration corresponding to the configuration of the fan-shaped radiation beam at its primary radiation path.

* * * * *